United States Patent [19] [11] 4,072,145
Silva [45] Feb. 7, 1978

[54] BRAIN WAVE SIGNAL SENSOR HEADBAND ASSEMBLY

[76] Inventor: Jose R. Silva, P.O. Box 1149, Laredo, Tex. 78040

[21] Appl. No.: 706,446

[22] Filed: July 19, 1976

[51] Int. Cl.² .............................................. A61B 5/04
[52] U.S. Cl. ................................. 128/2.1 E; 128/410; 128/418; 128/DIG. 4
[58] Field of Search ............... 128/2.06 E, 2.1 E, 404, 128/410, 411, 416, 417, 418, DIG. 4, 2.1 B

[56] References Cited

U.S. PATENT DOCUMENTS

| 2,943,628 | 7/1960 | Howell | 128/418 |
| 3,534,727 | 10/1970 | Roman | 128/2.06 E |
| 3,542,010 | 11/1970 | Love | 128/2.1 E |
| 3,882,850 | 5/1975 | Bailin | 128/2.1 B |
| 3,896,790 | 7/1975 | Dikmen | 128/2.1 B |
| 4,026,278 | 5/1977 | Ricketts et al. | 128/2.06 E |

FOREIGN PATENT DOCUMENTS 1,071,420  8/1954  France ............................. 128/2.1 B Primary Examiner—Ronald L. Frinks
Assistant Examiner—Lee S. Cohen
Attorney, Agent, or Firm—Bard, Springs, Jackson & Groves

[57] ABSTRACT

A headband assembly for sensing signals of brain wave frequencies of human subjects that includes an adjustable headband adapted to fit various sized heads, constructed to be quickly attached and detached by the wearer, and including electrodes that are shiftable along the headband and of a construction to penetrate the hair of the subject in making skin contact.

3 Claims, 3 Drawing Figures

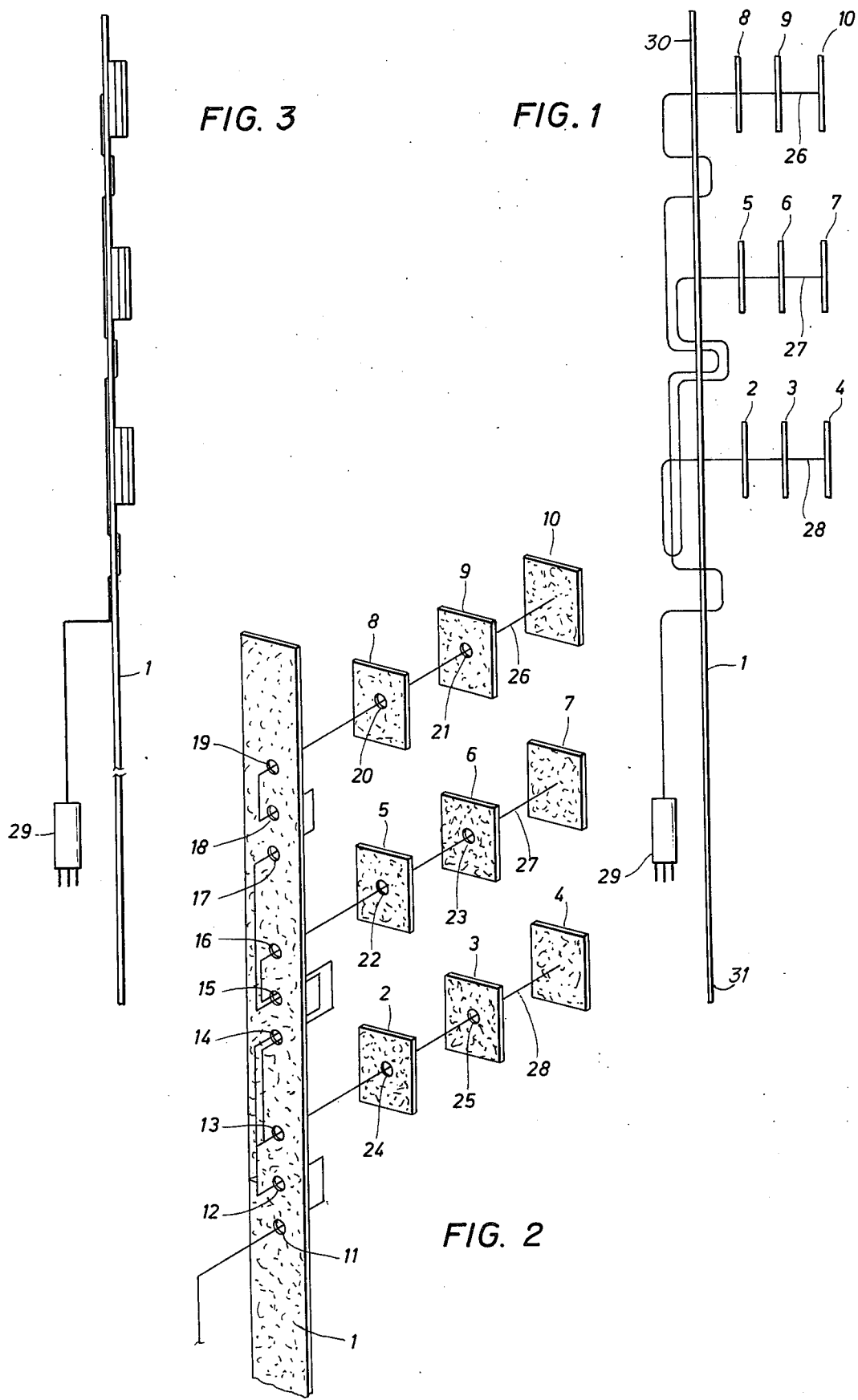

BRAIN WAVE SIGNAL SENSOR HEADBAND ASSEMBLY

BACKGROUND OF INVENTION

This invention relates to apparatus for measuring and correlating physiological and psychological performances of human subjects and the like, and more particularly relates to apparatus for measuring and correlating the brain wave frequency of a human subject with a preselected frequency sought to be attained.

It is well known that the human brain generates electrical pulsations at frequencies which are functionally related to mental and physical condition, and it is now well known that there are certain definite frequency ranges wherein the mental activity and capability of a person differs to a distinguishable degree. More particularly, the human brain provides pulsations in the "Beta Range" (above 14 cps) when a person is "wide awake" and in a normally active state, and that the frequency is in the "Delta Range" (below 4 cps) when the person is in a deep sleep or coma condition. When the brain wave frequency drops to zero, of course, the person is physiologically and mentally dead.

Between these two frequencies is the "Alpha Range," wherein the frequency rate falls between 7–14 cps, and the "Theta Range," wherein the rate is between 4–7 cps. The existence and significance of these ranges have only recently been recognized and are not fully understood, since no two human beings ever react exactly the same. It is now clearly apparent that when a person's brain wave frequencies are within the Alpha Range, a person is often imbued with significantly greater powers of concentration and a deeper inner awareness and frequently with an enhanced capacity for such powers as extrasensory perception and the like. Relatively little experimentation has been done with regard to the Theta Range, but subjects have sometimes exhibited extraordinary capabilities when in that state.

It has long been thought that various human physiological phenomena such as pulse and breathing rates, body temperature, skin resistivity and brain wave frequency are all non-volitional in character. In particular, therefore, it was believed that a person tends to drift between Beta and Delta in an entirely involuntary manner. For this reason, established scientific and medical opinion has, until recently, tended to look with skepticism on claims advanced on behalf of esoteric practices such as yoga, transcendental meditation, etc. Now, however, conditioning exercises have been devised and made available whereby an experienced practitioner of otherwise ordinary capacities can shift his brain wave frequency rate into the Alpha Range to obtain benefits such as those hereinbefore mentioned. Since these conditioning exercises are formulated and based on accepted scientific theory rather than on the more philosophical and metaphysical beliefs adhered to by practitioners of yoga and transcendental meditation, and since the effects obtained by such exercises are repeatable to a much greater degree, they are now widely accepted in conventional scientific circles.

Insofar as the measurement of human brain waves is concerned, it is old and well known, as evidenced by U.S. Pat. Nos. 3,662,746 and 3,623,477, to derive an electroencephalographical voltage signal indicative of such waves or pulsations. This signal may be visually or even audibly displayed, or it may be graphically recorded to provide what is popularly known as an "EEG." Thus, conventional detection and recording apparatus is used to monitor the subject using the aforementioned conditioning exercises in order to establish when and if the subject actually enters the Alpha state. For example, see the December 1972 issue of Electronics World, pp. 33–38, and also U.S. Pat. No. 3,548,812, for a fuller discussion of experimentation utilizing such measurements. See also U.S. Pat. Nos. 2,860,627, 3,662,746 and 3,658,054 for other discussions of conventional apparatus of this type.

The conditioning exercises hereinbefore referred to are comprised of a series of predetermined mental images which the subject or practitioner formulates according to prescribed sequence, and no external agency is actually required as such. Since the practitioner seldom if ever experiences any physical sensation when shifting to the Alpha state, some users of the exercises have practiced the technique while connected to electroencephalographic apparatus in order to indicate that the Alpha state has in fact been attained, as indicated in the aforementioned article in Electronics World. Further, in some cases the encephalographic signal has been translated into an audio output, whereby the frequency of the signal will inform and, to a limited extent, guide the practitioner in attaining the Alpha state. This technique is often of advantage in assisting or guiding a practitioner of limited experience and confidence. Nevertheless, the same audible signal which assists and guides the practitioner in descending out of the Beta Range is also a disadvantage when the practitioner approaches and enters the Alpha Range. A subject is not in a hypnotic state when in the Alpha Range, of course, and is still fully aware of his surroundings and in complete control of his faculties. Hence, the audible signal can often be a distraction which impedes rather than assists the practitioner at the very moment he is at the threshold of the Alpha Range.

Because of this disadvantage, it is conventional when utilizing the assistance of the audible representation of the practitioner's brain wave frequency to employ the assistance of another person to monitor the signal and disconnect it as the practitioner enters the Alpha Range. However, this is also undesirable for the obvious reason that the conditioning exercises are designed for self use, and it defeats the entire purpose of the technique if another person is required to be in attendance.

These and other disadvantages of the prior art are overcome with the present invention, and novel apparatus are herewith provided for monitoring and assisting the user of such conditioning exercises without the aid and attendance of another person.

SUMMARY OF INVENTION

In an ideal embodiment of the present invention, a headgear-type assembly of electrodes is provided for generating a train of electrical pulses or waves in functional relationship to the electrical pulses which are produced by the brain of the wearer of such electrodes.

Prior headgear-type assemblies of electrodes for sensing and measuring brain wave frequencies suffer from many disadvantages. Thus, many of the assemblies of the prior art are awkward and uncomfortable. Consequently, it is desirable to provide a headgear assembly that is easily manipulatable by the wearer thereof, and at the same time comfortable when placed in operative relationship to the head of the human subject.

Since the electrical pulses of the brain are of a very low amplitude, a good contact is necessary between the electrode and the skin. Hence, prior art assemblies have included the use of a cream or ointment in order to enhance the electrical contact between the skin and the electrode surfaces. This has proved to be objectionable, especially to persons who have a problem due to long hair. A further objectionable feature of the use of creams or ointments is in the area of hygiene. Thus, at the end of each cycle of use, it is necessary to thoroughly cleanse the electrode surface to remove the cream or ointment therefrom prior to reuse.

In the ideal embodiment of the present invention, however, there is provided a headgear sensor assembly that is easy to put on and take off. It can be located on the head of the wearer by the subject himself, and therefore assistance by others is not necessitated. Being of simple construction, the assembly disclosed herein is easier and less expensive to manufacture when considered in light of the somewhat complex nature of the headgear assemblies of the prior art.

A further advantage of the present headgear-type sensor assembly is that it can achieve good electrical contact between skin and electrode without the need of messy creams or ointments of the electrode sets of the prior art. Thus, the electrodes of the assembly of the present invention penetrate between the hairs of the head of the subject to make contact with the skin. Hence, metal prong electrode elements are so constructed and arranged as to readily penetrate between the subject's hair to contact the skin.

This prong-like construction of the electrodes results in a lower resistance at the point of contact with the skin, and thus reduced noise is introduced into the signal due to electrostatic, electrochemical or electrolytic factors. This is important since the signal is subject to very high amplification.

According to further advantages, the headband of the herein described assembly is easily adjustable to fit heads of various sizes, and therefore the subject is able to adjust and fit his own headband. Further, the electrodes are easily shiftable along the headband for better positioning of the electrodes about the head of the wearer. In addition, since no creams or ointments are required, there is never a need to clean creams or ointments from the electrodes.

It is therefore an object of the present invention to provide a new and advantageous signal sensor headband assembly for sensing brain wave frequencies.

It is also an object of the present invention to provide a headband assembly simple in construction and economical to manufacture.

It is a further object of the present invention to provide a headband assembly that is easy to handle, adapted to be quickly attached or detached in use, and adjustable in size.

It is another object of the present invention to provide a headband assembly that achieves better electrical contact between the electrodes thereof and the skin of the subject.

It is a further object of the present invention to provide an improved electrode for headband assemblies that penetrates the hairs of the subject to achieve skin contact.

It is a still further object of the present invention to provide an improved electrode for headband assemblies that is shiftable along the headband in various positions.

These and other objects, features and advantages of the present invention will become apparent from the following detailed description, wherein reference is made to the FIGURES in the accompanying drawings.

IN THE DRAWINGS

FIG. 1 is a simplified functional side view of one form of headband assembly embodying and suitable for practicing the concepts of the present invention, with the various parts shown in exploded fashion to facilitate the understanding of same;

FIG. 2 is a simplified functional front view of the form of headband assembly of FIG. 1 and also shown in exploded fashion; and FIG. 3 is a simplified functional side view of the headband assembly of FIGS. 1 and 2 with the parts disposed in operative relationship.

DETAILED DESCRIPTION

Referring now to FIGS. 1 and 2, there may be seen a simplified representation of a headband assembly embodying the concepts of the present invention and basically composed of a headbant unit, electrode assemblies and wiring therefor.

In particular, the headband 1 comprises an elongated strip of material of rectangular configuration. The strip is preferably constructed of a synthetic material which adheres when pressed together and sold under the trademark VELCRO. As is well known, this material includes a hook side and a loop side. When the hook side and loop side are brought together and pressed one against the other, the material adheres. To separate the hook and loop sides, it is simply necessary to pull the two apart. Thus, the strip in FIG. 1, for example, may be formed into a closed loop by pressing hook surface 30 against loop surface 31. As hereinbefore indicated, to separate the surfaces, it is simply necessary to pull the two surfaces 30 and 31 apart.

It should be readily apparent that strip 1 can therefore be easily formed into a headband for fitting about the head of a subject. Thus, by placing the strip 1 behind the head, the strip may be held to the head by wrapping the two ends around the head toward the face. It is then simply necessary to overlap the two ends so that surface 30 contacts surface 31, and to then press the two surfaces together. These two surfaces when pressed together adhere and thus hold the strip about the head of the subject. The degree of tightness of the strip about the head, of course, depends upon the wearer thereof, and upon the degree of overlap of the two terminal ends of the strip containing surfaces 30 and 31. To remove the headband, surfaces 30 and 31 are simply separated one from the other by pulling the overlapping end portion away from the lapped end portion. Headbands of this type, as is apparent, provide distinct advantages over prior art devices which included snaps, buttons and string members.

While surfaces 30 and 31 have been shown in FIG. 1 at each end portion of the strip headband 1, it is obvious that these two surfaces extend the full length of the strip, each occupying one side of the strip respectively.

In the preferred embodiment of the present invention, headband strip member 1 is preferably 27 inches long and ¾ inch wide. This length has been found suitable for accommodating heads of various sizes. Sufficient to say that the length of the strip must be capable of surrounding the circumference of the head of the wearer and providing an overlapping portion of the ends thereof for adherence.

Referring to FIG. 2, the headband strip member 1 is seen to include a plurality of openings therein indicated by numerals 11-19 for purposes which will be set forth hereinafter. The openings are each ¼ inch in diameter and are spaced 1⅛ inches apart from one another along the length of the strip 1.

Referring again to FIG. 2, three electrode assemblies are illustrated. The first assembly is indicated by numerals 2-4, the second by numerals 5-7, and the third by numerals 8-10. The spacer members 2, 3, 5, 6, 8 and 9 each include openings therein indicated by numerals 24, 25, 22, 23, 20 and 21, respectively. Numerals 4, 7 and 10 indicate the electrode of each assembly. Since each of the electrode assemblies is similar in construction, only one will be described in detail hereinafter.

Thus, assembly 2-4 comprises a first spacer member 2 rectangular in shape and constructed of VELCRO material. The opening 24 therein allows for passage of wire 28 therethrough. A second spacer member 3 is of the same construction as spacer 2 and includes opening 25 therein. The electrode element 4 is similarly of rectangular shape.

Electrode element 4 is constructed of VELCRO material that has been silver plated so as to be conductive. Due to the prong-like construction of the VELCRO material, the silver plating provides numerous elements capable of sensing brain wave frequencies when these prong-like elements are brought to bear against the skin of the subject. When applied to the head of the subject, these silver plated prong-like elements penetrate the hairs of the subject and make direct contact with the skin possible.

A flexible lead-shielded cable 28 is cemented to electrode element 4 at one end thereof. A preferable material for cementing cable 28 to element 4 is silver epoxy. Thus, the brain wave frequencies sensed by the silver plated prong-like members of element 4 are transmitted by cable 28 to a three-prong connector plug which is adapted to be coupled to a suitable measuring and correlating system, as hereinafter referred to. In a similar fashion, cables 26 and 27 of the other two assemblies are connected to plug 29.

In order to provide support for electrode element 4, it is preferred to cement spacer member 3 to electrode element 4 using silver epoxy. This joining of the elements 3 and 4 provides a backing member for the electrode element 4 and prevents element 4 from bending or flexing so as to not affect the conductive properties thereof.

In he preferred embodiment of the invention, the spacer elements 2 and 3 and the electrode element 4 are sized to about 2 inches in length and about ¾ inch in width.

Due to the adherent quality of the VELCRO material, it will be seen that by pressing elements 2, 3 and 4 together, a unitary assembly results, as depicted in FIG. 3. For example, this unitary assembly is further pressed against headband strip 1 to adhere the electrode assembly to the strip member 1. Accordingly, it is apparent that each of the three electrode assemblies may be shiftably located along the strip. To change the location of any one of the electrode assemblies, the assembly is pulled away from strip 1, moved along the strip to the desired location, and pressed back against strip 1 at the new location. The openings 11-19 and the slack in cables 26-28 allow for such movement of the electrode assemblies along the strip.

It should be noted that the headband assembly of the present invention is extremely lightweight and is therefore comfortable to wear. It is further of simple design and construction and is not awkward when placed about the head of the subject. The subject will find that it is easy to put on and take off and can be easily adjusted as to location and tightness. The prong-like construction and penetrating quality of the conductive electrodes eliminates the need for the messy creams and ointments of the prior art.

It will be readily apparent that various alternative types of components may be used to perform the various functions hereinbefore described. For example, while three electrode assemblies have been disclosed, it should be apparent that any convenient number of electrode assemblies may be located on the headband member. Three assemblies are practical, however, since one assembly is provided for each of the frontal, temporal and occipital lobes of the brain. In addition, other sizes and shapes of the strip, spacers and electrode elements may be used as well. Also, it will be apparent that other types of wiring systems may be used. While electrodes 4, 7 and 10 may be of the same construction as noted above, in a preferred embodiment the hook sides of elements 4 and 7 are silver plated, whereas in the case of element 10 the loop side thereof is silver plated.

The headband assembly disclosed and described above is particularly useful in conjunction with a system of measuring and correlating human physiological characteristics such as that depicted in U.S. Pat. No. 3,875,930, in the monitoring section thereof, although the herein disclosed headband assembly possesses utility in other similar systems as well.

Many other variations and modifications will readily become apparent to those having experience with assemblies of the type depicted and described herein. Accordingly, it should be clearly understood that the structures and techniques described herein and depicted in the accompanying drawings are illustrative only and are not intended as limitations on the scope of the present invention.

What is claimed is:

1. A headband for sensing human physiological characteristics and the like, comprising:
    an elongated strip of adherent material having a hook surface and a loop surface on opposite sides thereof, said strip being of a length sufficient to encircle the head of the wearer,
    at least one electrode of adherent material having a hook surface and a loop surface on opposite sides thereof,
    at least one spacer of adherent material having a hook surface and a loop surface on opposite sides thereof,
    one of said hook surface and said loop surface of the electrode being plated with an electrically conductive material,
    the other of said hook surface and said loop surface of the electrode being pressed against the mating one of the hook surface and the loop surface of said spacer, the other of said hook surface and said loop surface of the spacer being pressed against the mating one of the hook surface and the loop surface of said strip and being shiftable along the length of said strip, and
    means for electrically interconnecting said plated surface of said electrode with a measuring and a correlating system.

2. The headband of claim 1, wherein the hook surface of said electrode is plated.

3. The headband of claim 1, wherein the loop surface of said electrode is plated.

* * * * *